US011371922B2

(12) United States Patent
Rees et al.

(10) Patent No.: US 11,371,922 B2
(45) Date of Patent: *Jun. 28, 2022

(54) DEVICES, SYSTEMS AND METHOD FOR FLOORING PERFORMANCE TESTING

(71) Applicant: COLUMBIA INSURANCE COMPANY, Omaha, NE (US)

(72) Inventors: John J. M. Rees, Chattanooga, TN (US); Dennis J. Jones, Jr., Signal Mountain, TN (US); Thomas Jerry McClure, Jr., Acworth, GA (US); Chester A. Chaffin, Dalton, GA (US); Joseph M. Woodall, Ringgold, GA (US); Alan F. Buttenhoff, Tunnel Hill, GA (US)

(73) Assignee: COLUMBIA INSURANCE COMPANY, Omaha, NE (US)

( * ) Notice: Subject to any disclaimer, the term of this patent is extended or adjusted under 35 U.S.C. 154(b) by 119 days.

This patent is subject to a terminal disclaimer.

(21) Appl. No.: 16/861,693

(22) Filed: Apr. 29, 2020

(65) Prior Publication Data
US 2020/0309654 A1 Oct. 1, 2020

Related U.S. Application Data

(63) Continuation of application No. 15/674,083, filed on Aug. 10, 2017, now Pat. No. 10,684,204, which is a continuation of application No. 14/660,647, filed on Mar. 17, 2015, now Pat. No. 9,766,171.

(60) Provisional application No. 61/954,463, filed on Mar. 17, 2014.

(51) Int. Cl.
| *G01N 3/56* | (2006.01) |
| *G01N 33/36* | (2006.01) |
| *G01N 3/06* | (2006.01) |
| *G01N 3/307* | (2006.01) |
| *G01N 3/32* | (2006.01) |
| *G01N 21/25* | (2006.01) |
| *G01L 1/14* | (2006.01) |

(52) U.S. Cl.
CPC ............... *G01N 3/56* (2013.01); *G01L 1/146* (2013.01); *G01N 3/066* (2013.01); *G01N 3/307* (2013.01); *G01N 3/32* (2013.01); *G01N 21/25* (2013.01); *G01N 33/36* (2013.01); *G01N 2203/0058* (2013.01)

(58) Field of Classification Search
CPC .......... G01N 3/56; G01N 3/066; G01N 3/307; G01N 3/32; G01N 21/25; G01N 33/36; G01N 2203/0058; G01L 1/146
USPC ............................................... 73/7, 9, 12.01
See application file for complete search history.

(56) References Cited

U.S. PATENT DOCUMENTS

| 7,958,789 B2* | 6/2011 | Hayakawa | G06F 3/0445 73/862.626 |
| 2007/0171058 A1* | 7/2007 | Knowles | G08B 13/10 340/565 |
| 2007/0178274 A1* | 8/2007 | Federspiel | G01G 19/4142 428/95 |
| 2015/0009175 A1* | 1/2015 | Berget | G06F 3/0446 345/174 |
| 2015/0185909 A1* | 7/2015 | Gecnuk | G06F 1/324 345/174 |
| 2015/0276963 A1* | 10/2015 | Casimiro | G01V 3/088 324/658 |
| 2016/0217664 A1* | 7/2016 | Bradford | E04F 15/02 |
| 2018/0348073 A1* | 12/2018 | Biesheuvel | G01L 1/18 |

* cited by examiner

*Primary Examiner* — Eric S. McCall
(74) *Attorney, Agent, or Firm* — Ballard Spahr LLP

(57) ABSTRACT

In one implementation, a footfall detection assembly comprising a sensor underlayment unit and a data analysis device is provided. The sensor underlayment unit comprises a sensor having a unique sensor identifier and a plurality of zones, wherein the sensor is configured to measure zone capacitance in the plurality of zones, and a processing unit operably connected to the sensor. The processing unit is configured to receive the measured zone capacitance values from the sensor upon the occurrence of a change in measured zone capacitance of the sensor and generate and transmit a data packet comprising at least the unique sensor identifier and measured zone capacitance values upon occurrence of a change in capacitance of at least one of the plurality of zones of the sensor. The data analysis device is configured to receive the data packet, compare the measured zone capacitance values of the data packet to previously-measured zone capacitance values associated with the sensor underlayment into and generate a result therefrom.

20 Claims, 1 Drawing Sheet

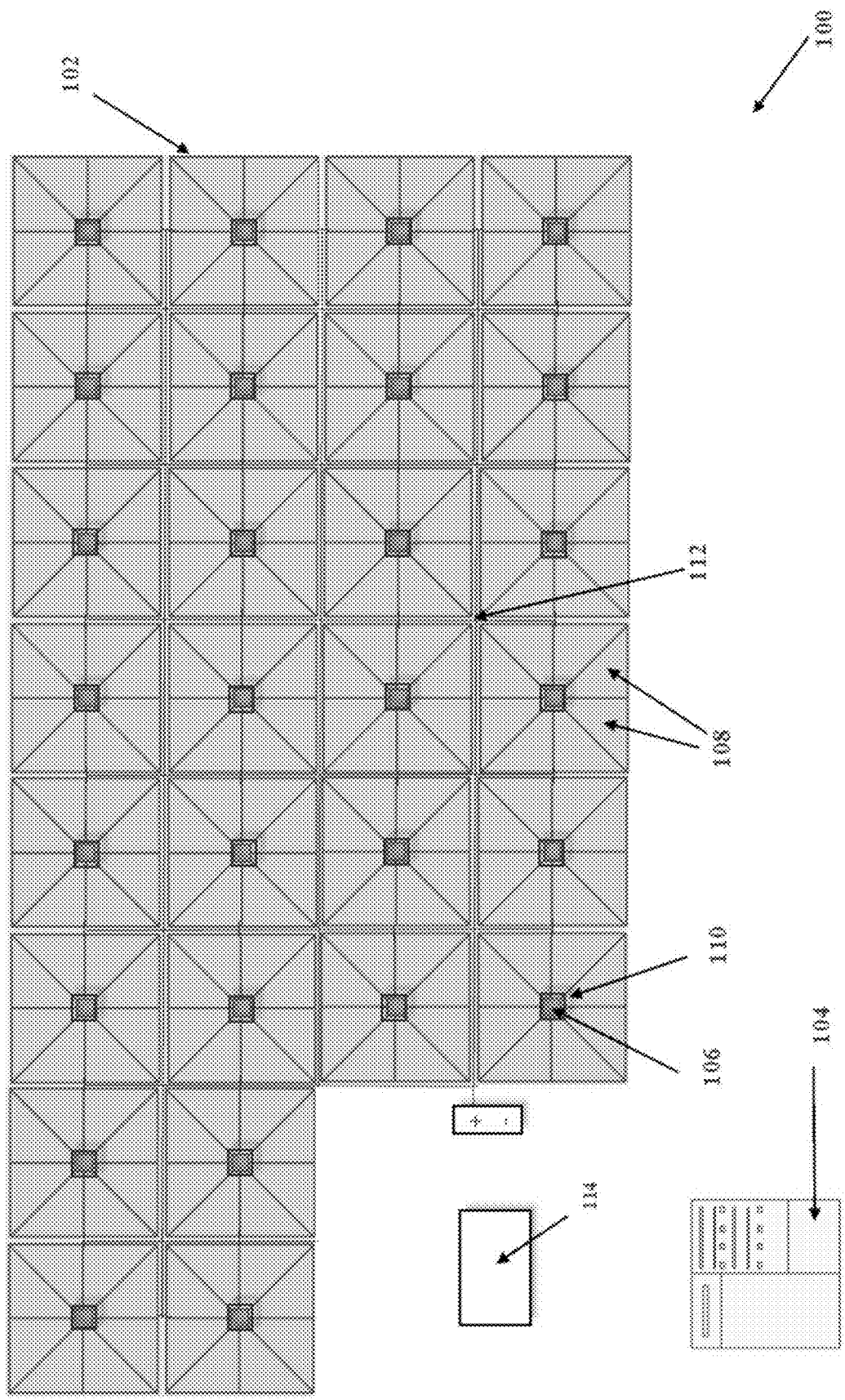

DEVICES, SYSTEMS AND METHOD FOR FLOORING PERFORMANCE TESTING

CROSS-REFERENCE TO RELATED APPLICATION

This application is a continuation of U.S. patent application Ser. No. 15/674,083, filed Aug. 10, 2017, which is a continuation of U.S. patent application Ser. No. 14/660,647, filed Mar. 17, 2015, now U.S. Pat. No. 9,766,171, which claims the benefit of the U.S. Provisional Application No. 61/954,463, filed Mar. 17, 2014. Each of these applications is incorporated herein by reference in its entirety.

BACKGROUND OF THE INVENTION

The Field of the Invention

Implementations described herein relate generally to a footfall detection assembly to measure flooring performance and useful life as well as associated systems and methods.

Background

Flooring performance testing is an important aspect of the flooring industry and, particularly, the carpeting industry. For example, carpets are generally expected to last from about 5 to about 10 years and are usually sold with a warranty based, at least partially, on the expected wear performance over time. Currently, wear testing is performed using either contract walking or mechanical tumblers. Contract walking involves lining a floor with a plurality of 9" by 22" carpet samples and having the contract walkers complete, e.g., 20,000 pedestrian laps over the plurality of samples. A contract walker will step in different locations on the 9"×22" sample as they do the walk test. While contract walking has the benefit of replicating real-world conditions, it is a costly and slow testing method. Mechanical tumbling, an alternative to contract walking, involves placing the carpet samples on the inner surface of a rolling drum and placing a weight inside that is configured to tumble on the carpet samples as the drum is rotated, thereby inducing wear. Mechanical tumbling is cheaper and faster than contract walking but does not readily correlate to real-world conditions. In either case, trafficked carpet samples are then graded, e.g. on a visual scale from 1-5. Such grading scales are subjective and do not lend themselves to clearly communicating the relative performance of different flooring samples.

Accordingly, a need exists for improved devices, systems and method for flooring performance testing that provide for improved accuracy in predicting field performance of flooring samples, that allow measurement at a reduced cost compared to current methods, and that enable effective comparisons between the performance of different flooring choices.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, the present disclosure provides for a footfall detection assembly comprising a sensor underlayment unit and a data analysis device. The sensor underlayment unit comprises a sensor having a unique sensor identifier and a plurality of zones, wherein the sensor is configured to measure zone capacitance in each of the plurality of zones, and a processing unit operably connected to the sensor and configured to receive the measured zone capacitance values from the sensor and generate and transmit a data packet comprising at least the unique sensor identifier and the measured zone capacitance values upon occurrence of a change in capacitance of the sensor and time stamp.

In another aspect, the present disclosure provides for a system for determining flooring performance comprising a plurality of sensor underlayment units, a data archival device configured to receive and store a data packet generated by the sensor underlayment unit and a data analysis device configured to receive the stored data packets, compare the zone capacitance to a previously measured zone capacitance values and generate a result therefrom.

In another aspect, the present disclosure provides for a method for determining flooring performance comprising installing a footfall detection assembly, installing a flooring for testing comprising a plurality of samples on top of the footfall detection assembly, providing a means for inducing foot traffic wear, removing one sample of the plurality of samples after a series of a selected numbers of foot strikes, measuring the one sample with at least one of a spectral measurement device and an imaging device at preselected angles to determine the viewing angle that produces the greatest color change as compared to a control sample, and determining the number of foot strikes the flooring sample can absorb until a threshold change in at least one of color and texture occurs.

In another aspect, the present disclosure provides for a method for measuring the number of foot strikes a flooring sample can absorb until a threshold change in at least one of color and texture occurs comprising providing a spectrometer having an incident light beam, providing a flooring sample for measurement, providing a control sample having a control pile direction, determining a flooring sample pile direction, orienting the flooring sample with respect to the spectrometer such that the incident light beam is preferentially oriented relative to the sample pile direction and measuring the flooring sample with the spectrometer at preselected angles to determining the viewing angle that produces the greatest color change as compared to the control sample.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate aspects and together with the description, serve to explain the principles of the methods and systems.

The FIGURE illustrates a schematic drawing of one implementation of a footfall detection assembly according to the present disclosure.

DETAILED DESCRIPTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of flooring performance testing have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

As used in the description and claims, references to "color change", "change in color" and variants thereof should be construed to include any color change between an untrafficked flooring sample and a trafficked flooring sample that is measurable by any technique known in the art, such as but not limited to, colorimetric methods, spectrophotometric methods, and the like. As used in the description and claims, references to "texture change", "change in texture" and variants thereof should be construed to mean any observable change in texture between an untrafficked flooring sample and a trafficked flooring sample and can include changes in texture due to damaged yarn tips, changes in yarn orientation relative to the flooring surface, and the like. As used in the description and claims, the term "appearance change" as applied to a flooring sample refers to a combination of the color change and texture change of a trafficked flooring sample relative to an untrafficked flooring sample.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be predefined, it is understood that each of these additional steps can be predefined with any specific aspect or combination of aspects of the disclosed methods.

Implementations described herein are directed toward, devices, systems and methods for flooring performance testing. In one aspect, 22 foot by 9 foot flooring comprising a plurality of flooring samples can be installed in a room for testing per applicable ASTM test methods. The flooring can be installed over a footfall detection assembly. The footfall detection assembly can comprise a sensor underlayment unit and a data analysis device. In one aspect, the sensor underlayment unit can comprise a sensor having a unique sensor identifier and a processing unit operably connected to the sensor. It is contemplated that the sensor can further comprise a plurality of zones, wherein the sensor is configured to measure zone capacitance in each of the plurality of zones. In other aspects, the processing unit can be configured to receive the measured zone capacitance values from the sensor and generate and transmit a data packet comprising at least the unique sensor identifier and measured zone capacitance values upon occurrence of a change in capacitance in at least one of the plurality of zones of the sensor. It is also contemplated that the data analysis device can be configured to receive the data packet, compared the measured zone capacitance values of the data packet to previously-measured capacitance values associated with the sensor underlayment unit and generate a result therefrom. It is contemplated that measured capacitance changes in each of the plurality of zones corresponds to at least one foot strike event. In one aspect, the sensor can be of the pressure plate type and, in a further aspect, multiples or arrays of these sensors can be installed in a grid pattern so the actual foot strike locations and total number of strikes per location can be measured, recorded and analyzed. In another aspect, the sensor can be a light curtain assembly configured to allow more precise locations of foot falls to be determined, as well as the total number of foot strikes per a given area in the walking space.

In yet other aspects, at least one of the plurality of samples can be processed through the above steps, using increments of foot traffic exposure, followed by measurement via an imaging device relative to an un-trafficked sample, in order to determine how many foot strikes the carpet can absorb without a noticeable change in at least one of color or texture. It is contemplated that the feedback from the above measurements can be used to improve flooring constructions with an emphasis on resistance to color and/or texture change induced by foot traffic. After the flooring sample is tested, it is contemplated that the resultant quality data can be used to improve the resiliency, wear-ability and life of the floor covering. In light of the present disclosure, one skilled in the art will appreciate that the resultant data can allow a floor covering manufacturer to optimize floor covering characteristics such as, for example and without limitation, twist levels, denier per filament, polymer types, fiber cross sections and the like in accordance with the present disclosure. In another aspect, the above measurements can be used as a communication tool to flooring customers, as a way to forecast the expected lifespan of a given floor covering product in relation to other floor covering products. In light of the present disclosure, one skilled in the art will appreciate that the footfall detection assembly and associated methods disclosed herein will enable a flooring manufacturer to more accurately engineer the usable life of a flooring, and allow warranties to better approximate the reality of wear and abrasion.

In the following description, numerous specific details are set forth in order to provide a thorough understanding described herein. It will be obvious, however, to one skilled in the art that the present disclosure may be practiced without these specific details. In other instances, well-known aspects of flooring performance testing have not been described in particular detail in order to avoid unnecessarily obscuring aspects of the disclosed implementations.

Turning now to the FIGURE, an implementation of one exemplary aspect of a footfall detection assembly is illustrated. In one aspect, a footfall detection assembly 100 having a sensor underlayment unit 102 and a data analysis device 104. The sensor underlayment unit 102 comprises a sensor 106 having a unique sensor identifier and a plurality of zones 108, wherein the sensor is configured to measure zone capacitance in each of the plurality of zones, and a processing unit 110 operably connected to the sensor 106 and configured to receive the measured zone capacitance values from the sensor and generate and transmit a data packet comprising at least the unique sensor identifier and the measured zone capacitance values upon occurrence of a change in capacitance of at least one of the plurality of zones of the sensor. In another aspect, the sensor underlayment unit can comprise a power supply bus 112 configured to supply the sensor 106 and processing unit 110 with power. In another aspect, the data analysis device 104 can be configured to receive the data packet, compare the measured zone capacitance values of the data packet to previously-measured zone capacitance values associated with the sensor underlayment unit and generate a result therefrom. It is also contemplated that the processing unit 110 can be configured to wirelessly transmit the data packet to the data analysis device 104 and that the data analysis device can further comprise a wireless receiver operable to receive the data packet. In an alternative aspect, it is contemplated that the data analysis device can comprise a radio frequency (RF) data logger and the processing unit can be configured to transmit the data packet to the data analysis device via RF.

In one aspect, the sensor 106 can be a capacitance sensor and, in further aspects, can be a pressure plate capacitance sensor. In other aspects, the sensor can comprise an array of sensors. In light of the present disclosure, one skilled in the art will also appreciate that other sensor types such as, for example and without limitation, capacitance thin film, retro-reflective optical, force sensitive resistor, membrane keyboard, piezoelectric thin film, hall effect, surface acoustic wave, strain gauge, pressure switch sensors and the like can be employed in lieu of pressure plate capacitor sensors without departing from the scope of the present disclosure.

In another aspect, the sensor 106 can comprise a plurality of zones 108. Here, the sensor can be configured to measure zone capacitance in each of the plurality of zones. In order to reduce the overall cost of the system, the required data storage capacity and the real-time data processing speed, the number of sensors per meter can be chosen to be relatively small and, in a further aspect, can be less than about 10. It is also contemplated that, in more complicated systems, sensors could be as numerous and as small as the pixels of, e.g., a computer or TV screen. In another, it is contemplated that each sensor can comprise from about 2 to about 12 zones, more preferably, from about 4 to about 10 zones, and, most preferably, about 8 zones. In another aspect, the plurality of zones can be equally sized. In a further aspect, the zones can be spaced radially about a center point and, optionally, can be equally sized. It is further contemplated that each of the plurality of zones can cover substantially equal radial portions as measured from the center of the area of the sensor underlayment unit. It is contemplated that the sensor underlayment unit can cover an area of from about 0.05 to about 0.50 square meters and, preferably, about 0.25 square meters. In operation, the sensor can measure zone capacitance in each of the plurality of zones. In certain aspects, the sensor can have a footprint of from about 1 to about 144 square inches. In further aspects, the sensor can have a side or diameter from about 1 to about 12 inches.

In another aspect, a data analysis device 104 can be configured to compare the time stamp of the data packet to the time stamp of at least one other data packet to confirm whether a foot strike is unique or associated with the at least one other data packet. It is further contemplated that the data analysis device is programmed to determine if the measured zone capacitance values are a result of a singular external event or a plurality of external events. Here, the data packet further comprises time values that correspond to the respective measured zone capacitance values. In operation, if the time values of respective measured zone capacitance values are less than a predetermined time value, the data analysis device is configured to generate a singular footfall event result. The predetermined time value can be from about 10 to about 500 msec, more preferably, from about 20 to about 250 msec, and, most preferably, from about 35 to about 50 msec. However, one skilled in the art will appreciate that the predetermined time value depends on the sensor technology used and, even further, the rate at which a given sensor can return to equilibrium.

In another aspect, the data packet can further comprise an area identifier. In light of the present disclosure, one skilled in the art will appreciate that an area identifier can be used when a plurality of sensor underlayment units are used together in a system.

It is also contemplated that the footfall detection assembly can comprise a data archival device 114 configured to receive and store each data packet transmitted by the sensor underlayment unit 102. It is contemplated that the data archival device can be operably associated with the data analysis device or independent from the data analysis device. In one aspect, the data archival device can comprise a RF data logger. In another aspect, the data archival device can comprise a computer data storage medium such as an SD card, a thumb drive, a dongle and the like. The data archival device can be further configured to transmit a plurality of stored data packets to the data analysis device 104 in a periodic batch operation via, for example and without limitation, a local-area network and the like.

In yet other aspects, it is contemplated that a plurality of sensors 106, the processing unit 108, the data analysis device 104, and, optionally, the data archival device 114 can be integrated into one device. However, one skilled in the art will appreciate that the present disclosure does not require that the sensor 108, the sensor processing unit 108, the data archival device 114, and the data analysis device 104 or any other component be constrained to separate physical entities. Accordingly, in this or any aspect disclosed herein, the components of the footfall detection assembly and systems thereof can take on a variety of implementations and all such implementations are within the scope of the present disclosure.

In yet other aspects, it is contemplated that a plurality of sensor underlayment units 102 can be employed in a system for determining flooring performance. Here, it is contemplated that a power supply bus can be operably connected to each of the sensor underlayment units. Here, a data archival device can be configured to receive and store data packets transmitted by each of the plurality of sensor underlayment units. In another aspect, a data analysis device can be configured to receive the stored data packets, compare the measured zone capacitance values associated with one of the plurality of sensor underlayment units to previously-measured zone capacitance values transmitted by the same sensor underlayment unit and generate a result therefrom. In a further aspect, the data archival device and the data analysis device can be embodied in the same physical entity.

In another implementation of the present disclosure, a system for determining flooring performance is provided. The system for determining flooring performance comprises a plurality of sensor underlayment units wherein each sensor underlayment unit further comprises a sensor and processing unit as described previously and a power supply bus configured to supply the plurality of sensor underlayment units with power. Additionally, the system comprises a data analysis device configured to receive data packets originating at each of the plurality of processing units as well as compare the measured zone capacitance values from each of the plurality of sensors with previously-measured zone capacitance values transmitted by the same sensor underlayment unit and generate a result therefrom. Optionally, the system for determining flooring performance can comprise a data archival device configured to receive and store the data packet and as described previously.

In another aspect, it is contemplated that the system for determining flooring performance can comprise a sensor underlayment unit comprising a plurality of sensors and a processing unit operably connected to the plurality of sensors, as described previously.

In operation, for example, a 22 foot by 9 foot flooring comprising a plurality of flooring samples can be installed in a room for testing per applicable ASTM test methods. Here, a system for determining flooring performance can be installed beneath the flooring in a grid pattern so the actual foot event locations and total number of footfall events per location can be measured and recorded. The untrafficked flooring samples can be measured on an imaging device at at least one preselected viewing angle prior to testing. It is further contemplated that the imaging device can comprise, for example and without limitation, a camera, a flatbed scanner, a spectrometer, a laser scanner and the like. In operation, the flooring sample can be subjected to a selected number of foot strikes, followed by measurement and comparison relative to the un-trafficked flooring sample, in order to determine how many foot strikes the carpet can absorb without a noticeable change in color or texture.

In another aspect, the threshold change in at least one of color and texture can be measured using at least one of spectral and image analysis of the flooring sample both before and after the induced foot traffic wear. In light of the present disclosure, one skilled in the art will recognize and appreciate that this comparison can be, for example and without limitation, a spectral color change analysis such as DECMC, a photo-based pixel comparison, a 3-D image and depth analysis, and the like. In another aspect, the threshold change in at least one of color and texture can be about 2.0 DECMC units.

In another aspect, the change in at least one of color and texture can be expressed as a percentage relative to the measurements of the untrafficked flooring samples. Here, using the RGB color space method to illustrate, a selected group of pixels corresponding to substantially identical locations on the untrafficked and trafficked samples can be averaged and compared. In one aspect, the maximum of each value (i.e., R, G, and B) can be subtracted from the minimum of each value, then summed and expressed as a % change relative to the values measured for the untrafficked sample alone. It is contemplated that a threshold change as expressed as a % change relative to the measured values for the untrafficked sample can be from about 5% to about 25%.

In another aspect, a spectrometer can be used as the imaging device. Here, the spectrometer can comprise a non-contact spectrometer. It is contemplated that the non-contact spectrometer can be configured to measure the L, a, and b color values of each flooring sample. Control samples can be unworn samples of the same flooring type as the flooring sample and can be used to determine a delta L, a delta a, and a delta b as well as a DECMC 2:1 value.

Accordingly, the FIGURE and the corresponding text provide a number of different components and mechanisms for determining flooring performance. In addition to the foregoing, implementations described herein can also be described in terms acts and steps in a method for accomplishing a particular result. For example, a method for determining flooring performance is described with reference to the components and diagrams of the FIGURE.

Here, a method for determining flooring performance can comprise installing a foot strike detection assembly; installing a flooring for testing comprising a plurality of flooring samples on top of the foot strike detection assembly; measuring a selected untrafficked sample with an imaging device at at least one preselected angle; providing a means for inducing foot traffic wear; subjecting the selected flooring sample to a selected number of foot strikes; measuring the selected trafficked sample with a an imaging device at the at least one preselected angle; comparing the selected untrafficked sample measurements to the selected trafficked sample measurements; and determining the number of foot strikes the selected sample can absorb until a threshold change in at least one of color and texture occurs. In a further aspect, the method can further comprise the step of improving carpet construction to improve resistance to color and texture change induced by foot traffic. In another further aspect, the method can further comprise forecasting the expected lifespan of the tested flooring in relation to other flooring products. In a further aspect, the means for inducing foot traffic wear can be, for example and without limitation, a human walker walking on the flooring to induce foot traffic wear, at least one robotic foot walking on the flooring to induct foot traffic wear, and the like.

In other implementations, the present disclosure provides for a method for measuring the number of foot strikes a flooring sample can absorb until a threshold change in at least one of color and texture occurs comprising providing a spectrometer having an incident light beam, providing a flooring sample for measurement, providing a control sample having a control pile direction, determining a flooring sample pile direction, orienting the flooring sample with respect to the spectrometer such that the incident light beam is preferentially oriented relative to the sample pile direction, measuring the flooring sample at preselected angles to determine the viewing angle that produces the greatest color change as compared to the control sample. In a further aspect, the preselected angles can be 22.5 degrees, about 30.0 degrees, and about 45.0 degrees. In even further aspects, the measurement can be repeated with differing pile directions. Additionally, the method can further comprise a laser scanning apparatus known in the art to map the worn carpet topography and calculate loss of height and tuft integrity.

Thus, implementations of the foregoing provide various desirable features. For instance, the foot strike detection assembly and associated methods can reduce testing cost and produce results that are more accurate with regard to real-world use. In another instance, an improved method of measuring and comparing relative flooring sample performance is provided that provides consistent and repeatable readings to determine flooring wear.

The present invention can thus be embodied in other specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A system comprising:
a floor covering disposed in an area; and
a sensor underlayment unit disposed below the floor covering and comprising:
a plurality of sensors, wherein each sensor of the plurality of sensors has a plurality of zones associated therewith and is configured to measure a value of at least one parameter in at least one of the plurality of zones associated therewith; and
a processing unit communicably coupled to the plurality of sensors and configured to receive the value of the at least one parameter and generate and transmit a data packet comprising the value of the at least one parameter upon occurrence of a change in the value of the at least one parameter in the at least one of the plurality of zones associated with at least one of the plurality of sensors; and
a data analysis device configured to receive the data packet and determine an event of a footfall on the floor covering in the area and a location of the footfall in the area based on the value of the at least one parameter of the data packet.

2. The system of claim 1, wherein to determine the event of a footfall, the data analysis device is configured to compare the value of the at least one parameter of the data packet to previously-measured parameter values associated with the sensor underlayment unit.

3. The system of claim 1, wherein the plurality of sensors are arranged in a grid pattern.

4. The system of claim 1, wherein the plurality of sensors are arranged in a light curtain assembly.

5. The system of claim 1, wherein the plurality of sensors comprise less than 10 sensors per square meter of the area.

6. The system of claim 1, wherein the data analysis device is further operable to forecast an expected lifespan of the floor covering based on the value of the at least one parameter value and previously-measured parameter values associated with the sensor underlayment unit.

7. The system of claim 1, wherein the data analysis device is further operable to predict field performance of the floor covering based on the value of the at least one parameter and previously-measured parameter values associated with the sensor underlayment unit.

8. The system of claim 1, wherein a footprint of each sensor of the plurality of sensors ranges from about 1 square inch to about 144 square inches.

9. The system of claim 1, wherein the plurality of zones comprises 2 to 12 zones.

10. A system comprising:
a floor covering disposed in an area; and
a sensor underlayment unit disposed below the floor covering and comprising:
a sensor having a unique identifier and a plurality of zones, the sensor being configured to measure at least one parameter value in at least one of the plurality of zones; and
a processing unit operably coupled to the sensor and configured to receive the at least one parameter value and generate and transmit a data packet comprising the at least one parameter value from the sensor and generate and transmit a data packet comprising at least the unique identifier of the sensor and the at least one parameter value; and
a data analysis device that is communicably coupled to the processing unit and configured to receive the data packet, and compare the at least one parameter value of the data packet to previously-measured parameter values associated with the sensor underlayment unit to determine an event of a foot strike on the floor covering in the area and that the foot strike is a unique foot strike.

11. The system of claim 10, wherein the data analysis device is configured to transmit the data packet upon occurrence of a change of the at least one parameter value in the at least one of the plurality of zones of the sensor.

12. The system of claim 10, wherein the sensor comprises at least one of a pressure plate capacitance sensor, a capacitance thin film sensor, a retro-reflective optical sensor, a force sensitive resistor sensor, a membrane keyboard sensor, a piezoelectric thin film sensor, a hall effect sensor, a surface acoustic wave sensor, a strain gauge sensor, or a pressure switch sensor.

13. The system of claim 10, wherein the data analysis device is further operable to forecast an expected lifespan of the floor covering based on the at least one parameter value and previously-measure parameter values associated with the sensor underlayment unit.

14. The system of claim 10, wherein to determine whether the foot strike is unique, the data analysis device is configured to compare a time stamp of the data packet to a time stamp of at least one other data packet comprising the previously-measured parameter values.

15. A system comprising:
a sensor underlayment unit, comprising:
a plurality of sensors, wherein each sensor has a unique sensor identifier and a plurality of zones, wherein each of the plurality of sensors is configured to measure a value of at least one parameter in at least one of the plurality of zones; and
a processing unit operably connected to the plurality of sensors and configured to receive the value of the at least one parameter from at least one of the plurality of sensors and generate and transmit a data packet comprising at least the unique identifier and associated value of the at least one parameter from at least one of the plurality of sensors upon occurrence of a change in the value of the at least one parameter of that sensor;
a data archival device configured to receive and store the data packet transmitted by the sensor underlayment unit; and
a data analysis device configured to compare the value of the at least one parameter from the data packet to previously-measured parameter values associated with the same sensor and generate a result therefrom.

16. The system of claim 15, further comprising a power supply bus operably connected to the sensor underlayment unit.

17. The system of claim 15, wherein the processing unit is configured to wirelessly transmit the data packet.

18. The system of claim 15, wherein the data archival device further comprises a wireless receiver.

19. The system of claim 15, wherein the data analysis device is operable to determine if the value of the at least one parameter is the result of a singular external event.

20. The system of claim 15, wherein the plurality of zones comprises from about 2 to about 8 zones.

* * * * *